United States Patent [19]

Breslau et al.

[11] 4,432,350
[45] Feb. 21, 1984

[54] MEANS FOR APPLYING TOPICAL ANESTHESIA FOR USE WITH A LARYNGOSCOPE

[76] Inventors: Alan J. Breslau, 11 Rust Hill Rd.; Bernard Broad, 2 Silverbell Rd., both of Levittown, Pa. 19056

[21] Appl. No.: 255,125

[22] Filed: Apr. 17, 1981

[51] Int. Cl.³ .............................................. A61B 1/24
[52] U.S. Cl. ..................... 128/10; 128/15; 128/17
[58] Field of Search .................... 128/10-20, 128/3-4, 200.14-200.15, 200.21-200.22, 200.26, 204.18, 205.13-205.16, 207.14, 207.26, 207.28, 203.12, 203.19, 203.23-203.24, 203.28, 232, 276, 278; 604/36-37, 214

[56] References Cited

U.S. PATENT DOCUMENTS

| | | | |
|---|---|---|---|
| 480,787 | 8/1892 | Scott | 128/266 |
| 1,023,042 | 4/1912 | Scott | 128/232 |
| 1,618,971 | 3/1927 | De Zeng | 128/16 |
| 2,070,820 | 2/1937 | Allyn | 128/11 |
| 2,289,226 | 7/1942 | Von Foregger | 128/16 |
| 2,433,705 | 12/1947 | Palmeter | 128/10 |
| 2,435,400 | 2/1948 | Long | 128/11 |
| 2,630,114 | 3/1953 | Hart | 128/11 |
| 3,595,222 | 7/1971 | Vellacott et al. | 128/11 |
| 3,986,854 | 10/1976 | Scrivo et al. | 65/4 R |
| 4,126,127 | 11/1978 | May | 128/11 |
| 4,195,624 | 4/1980 | Douglas | 128/8 |
| 4,295,465 | 10/1981 | Racz et al. | 128/16 X |
| 4,314,551 | 2/1982 | Kadell | 128/11 |

FOREIGN PATENT DOCUMENTS 1278067 9/1968 Fed. Rep. of Germany ........ 128/10
115785 8/1968 Norway .............................. 128/10

*Primary Examiner*—Lee S. Cohen
*Assistant Examiner*—Angela D. Sykes
*Attorney, Agent, or Firm*—Frederick A. Zoda; John J. Kane

[57] ABSTRACT

A laryngoscope is disclosed of a conventional configuration having a blade handle which includes a device for the applying of topical anesthesia as the blade of the laryngoscope is inserted into the pharynx and larynx of a patient. The application device includes a reservoir for holding an amount of topical anesthesia within a fluid chamber defined therein. The reservoir may be attached detachably with respect to a handle of a laryngoscope, or may be a contiguous and inherent part thereof. A supply conduit being in fluid flow communication with the fluid chamber extends outwardly from the reservoir such that topical anesthesia may be caused to flow therethrough. A retainer holds the supply conduit in the proper position adjacent to a blade of the laryngoscope in such a fashion that the tip of the conduit is adjacent to the forwardly extending portion of the blade to facilitate the application of topical anesthesia in the area immediately forward of the blade. In this manner the pharynx may be anesthetized and the topical anesthesia sprayed directly into the larynx, producing anesthesia of the mucosa and vocal cords. The reservoir may be of a permanent nature or detachably securable such as to be a throw-away unit and the walls thereof are preferably of a soft material to allow compression thereof by the hand of the anesthesiologist while gripping the handle of the laryngoscope.

16 Claims, 7 Drawing Figures

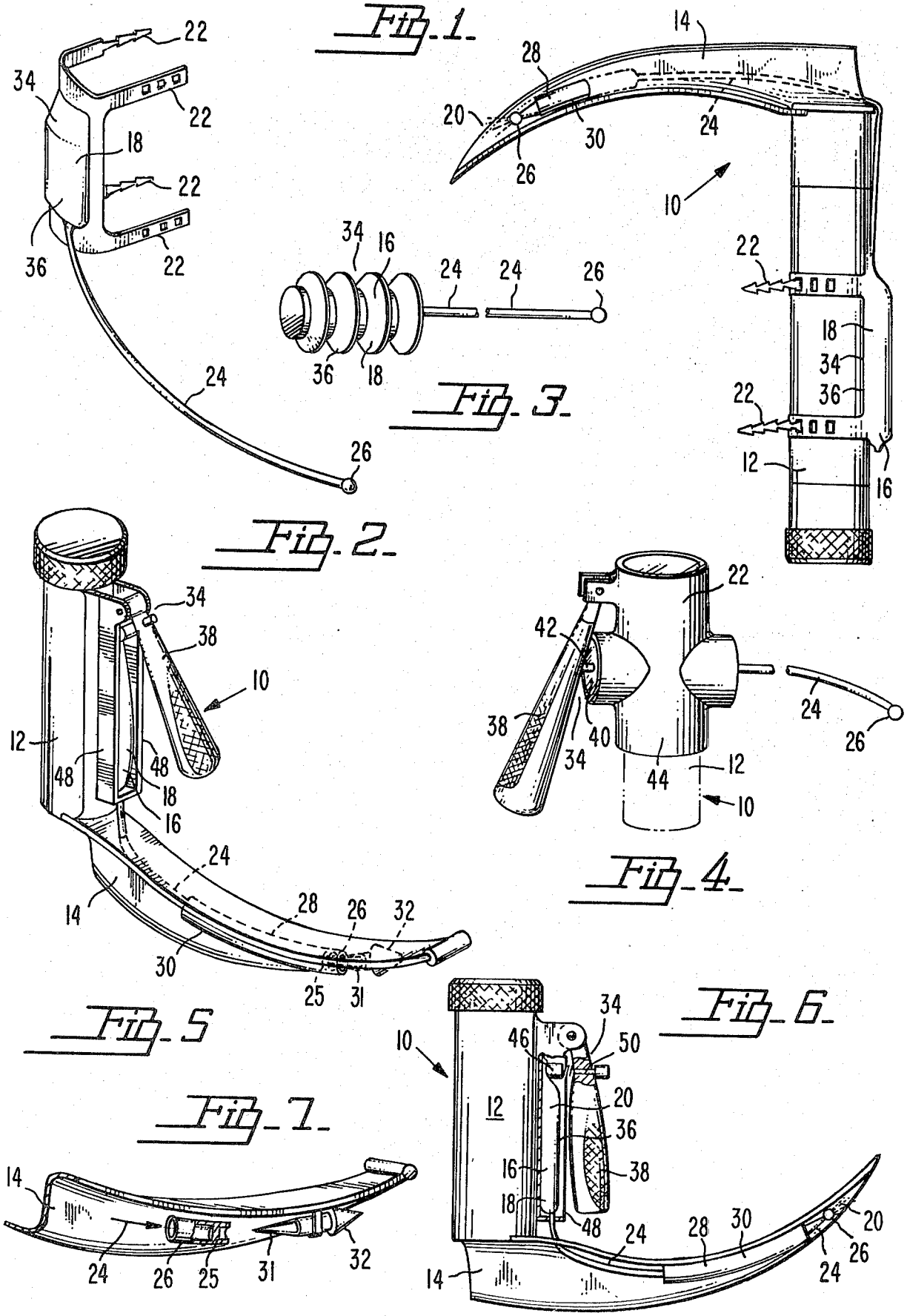

MEANS FOR APPLYING TOPICAL ANESTHESIA FOR USE WITH A LARYNGOSCOPE

BACKGROUND OF THE INVENTION

1. Field of the Invention

During the course of many anesthetic procedures it is necessary for an anesthesiologist or the anesthetist to insert an endotracheal tube in order to establish and protect an airway. Often it is also necessary to place other tubes and devices down the pharynx, larynz and esophagus of the patient in accordance with the specific procedure being performed.

For this purpose a device called a laryngoscope is inserted into the oral cavity to expose the structure of the pharynx and larynz. There are a number of different designs and configurations for such laryngoscopes, but generally they include a handle and a blade area. The blade area is inserted into the pharynz of the patient and often tubes or other devices are placed through this blade area in order to visualize or otherwise treat the larynx of the patient. Often the laryngoscope blade contains a light wherein the handle is used as the receptacle and holder for the batteries.

Usually, the anesthesiologist sprays the pharynx and the larynx with a topical anesthetic such as lidocaine from a hypodermic syringe, an aerosol container or other such devices. This operation requires usage of both hands with one on the laryngoscope and one applying the topical anesthetic. It is desirable to permit such an anesthesiologist to perform both functions with a single hand so as to allow freedom of movement of the other hand to perform other necessary and desirable functions during the time of insertion of te laryngoscope.

2. Description of the Prior Art

Many prior art devices have been used for attachment to laryngoscopes for various purposes. However, no devices shown or disclosed which include an easily disposable means for the supplying of topical anesthetic to the area immediately during insertion of the blade of a laryngoscope. Examples of such prior art devices are shown in U.S. Pat. Nos. 480,787; 1,618,971; 2,070,820; 2,289,226; 2,435,400; 2,630,114; 3,595,222; 3,986,854; 4,126,127; and 4,195,624.

SUMMARY OF THE INVENTION

The present invention provides a means for applying topical anesthesia when using a larynoscope having a conventional blade and handle configuration, or a new design which incorporates the means for applying topical anesthesia as an inherent component of its configuration. The means for application includes a reservoir means adapted to contain a topical anesthesia fluid therein. This reservoir means may be detachably secured with respect to the handle of a laryngoscope or integral therewith. The reservoir means defines a fluid chamber therein which is adapted to actually hold the topical anesthesia fluid. An attachment means such as a wire tying means or the like may be used to connect the reservoir means with respect to the handle of the laryngoscope.

A supply conduit means preferably being integral with respect to the reservoir means is included. This supply conduit means extends outwardly from the reservoir and is in fluid flow communication with the interior of the fluid chamber such that it is adapted to receive topical anesthetic fluid therefrom upon delivery such as by compression of the reservoir means. The supply conduit includes a conduit tip located at the end of the supply conduit opposite from the point of attachment with respect to the reservoir means. This conduit tip is adapted to release topical anesthetic received from the supply conduit means.

The supply conduit is preferably held to the blade of the laryngoscope by a retainer means which is attached to the blade and is adapted to receive the supply conduit means extending therethrough. Preferably this retainer means is tubular in configuration.

The means for applying topical anesthesia also includes a delivery means which may take a variety of forms but is generally engageable with respect to the topical anesthetic fluid to cause it to be expelled from the fluid chamber through the supply conduit means for release through the conduit tip means. This delivery means may comprise merely a compressible outer wall area of the reservoir means such that the exertion of pressure on the wall area will cause movement of the topical anesthetic through the supply conduit.

The application means may also include a dispensing nozzle secured to the blade means of the laryngoscope and adapted to receive the conduit tip means secured thereto to control the release of topical anesthetic from the supply conduit means. In this manner more effective control of the dispensing of topical anesthetic in the forward area of the laryngoscope blade will be achieved.

In an alternative configuration a lever actuator means may be pivotally secured with respect to the handle of a laryngoscope to be adapted to pivot into abutting contact with respect to the reservoir means to thereby expel topical anesthetic therefrom by the exertion of pressure thereon. To facilitate this expulsion a piston member may be included in the level actuator means to actually contact the reservoir means and expel the fluid.

The reservoir means may take the form of a simple collapsible bag of soft material or it may be a bellows-type configuration. Also alternatively, the application means may include a sleeve means which is selectively securable about the handle of the laryngoscope with a lever actuator means pivotally secured with respect thereto. With this configuration it is also possible to use a spring biased retainer bar which is secured with respect to the lever actuator means to thereby hold the reservoir means in contact with the handle means during movement of the lever actuator means forward and backward.

It is an object of the present invention to provide an application device which may be an integral part of a laryngoscope or be an adjunct part with respect thereto.

It is an object of the present invention to provide a means for applying topical anesthesia for use with a laryngoscope which may upon the activation of a triggering mechanism spray a sufficient quantity of topical anesthesia or other fluid material into the pharynx and larynx in order to anesthetize these areas prior to insertion of an endotracheal tube.

It is an object of the present invention to provide a means for applying topical anesthesia which includes a reservoir which may be a membraneous pouch such as a polyethelene or polyethelene/polyester laminated pouch or other suitable plastic film or membrane.

It is an object of the present invention to provide a means for applying topical anesthesia which is disposable after each usage of the laryngoscope.

It is an object of the present invention to provide a means for applying topical anesthesia which includes a dispensing nozzle fixedly secured with respect to the blade of the laryngoscope which effectively controls the dispensing of the topical anesthesia in the area immediately forward of the entering laryngoscope blade.

It is an object of the present invention to provide a laryngoscope which includes a means for applying topical anesthesia which is capable of operation by an anesthesiologist or an anesthetist with only one hand.

It is an object of the present invention to provide a laryngoscope which includes a disposable chamber for the retaining of topical anesthesia therein.

It is an object of the present invention to provide a device for the automatically applying of topical anesthesia to a pharynx and larynx upon insertion of a laryngoscope which dispenses the topical anesthesia merely by the compression of a lever, pushing of a piston, or pressing of a button to permit a pressurized gas to exert pressure on the pouch of anesthetic or force it out of a rigid chamber, or activate a pump, actuated by pressurized gas, electricity or other means, to cause the anesthetic to flow to the dispensing tip.

BRIEF DESCRIPTION OF THE DRAWINGS

While the invention is particularly pointed out and distinctly claimed in the concluding portions herein, a preferred embodiment is set forth in the following detailed description which may be best understood when read in connection with the accompanying drawings, in which:

FIG. 1 is a side elevation of an embodiment of a laryngoscope employing the means for applying topical anesthesia of the present invention;

FIG. 2 is a perspective illustration of an embodiment of the means for applying topical anesthesia of the present invention;

FIG. 3 is a perspective illustration of an alternative embodiment of the means for applying topical anesthesia of the present invention;

FIG. 4 is a perspective illustration of still another embodiment of the means for applying topical anesthesia of the present invention;

FIG. 5 is a perspective illustration of an embodiment of a means for applying topical anesthesia utilizing a lever actuator;

FIG. 6 is a side view of another embodiment of the means for applying topical anesthesia of the present invention utilizing a lever actuator; and FIG. 7 is a side illustration of an embodiment of a dispensing nozzle as used in the present invention.

DETAILED DESCRIPTION OF THE PREFERRED EMBODIMENT

The present invention provides a means for the applying of topical anesthesia specifically for use with a laryngoscope 10 which includes a handle means 12 and a blade means 14. There are a variety of different shapes and sizes of laryngoscopes, however, they all do include the basic handle and blade configuration.

The present invention includes a reservoir means 16 which is adapted to be secured to the handle area 12 in a detachable fashion. The reservoir defines a fluid chamber 18 therein adapted to hold the topical anesthetic fluid 20. The reservoir 16 and chamber 18 are secured with respect to the handle 12 by a suitable attachment means 22. This attachment means can take the form of a plastic tie-strap as shown in FIGS. 1 and 2 or any other type of convenient attachment means.

A supply conduit means 24 is included in fluid flow communication with the fluid chamber 18. In this manner the supply conduit means 24 is adapted to receive the topical anesthetic fluid 20 therethrough upon urging of the fluid out of chamber 18. The conduit 24 carries this expelled fluid to the opposite end thereof at the conduit tip means 26. A dispensing nozzle 32 may be included fixedly secured with respect to the blade 14 of the laryngoscope 10. In this configuration the conduit tip means 26 is secured to the dispensing nozzle as shown in FIG. 7 and the dispensing nozzle achieves accurate and effective spraying of the fluid 18. The dispensing nozzle 32 includes a perforating needle point 31 extending rearwardly therefrom. Also, the supply conduit means 24 includes a sealing membrane 25 extending thereover which is adapted to be perforated when the conduit tip means 26 is placed over the needle point 31. In this manner the membrane will be pierced and the seal will be perforated allowing fluid flow communication between the interior of the supply conduit means 24 and the dispensing nozzle 32.

Preferably the supply conduit means 24 is secure with respect to the blade 14 of laryngoscope 10 by way of a retainer means 28. This retainer may take any form but preferably is a tubular member 30.

In order to effectively cause the fluid 20 to pass through the supply conduit means 24 a delivery means 34 must be included in the present application means. One of the simplest ways of providing this delivery means is to form the reservoir means 16 with a compressible outer wall area 36. This may take the form of a bellows configuration as shown in FIG. 3 or merely a pliable and compressible pouch configuration as shown in FIGS. 1 and 2. Alternatively, a lever actuator means 38 can be included as shown in FIGS. 5 and 6 which can be squeezed by the fingers or palms of the anesthetist during insertion of the laryngoscope to cause compression of the fluid chamber 18 with the resulting expelling of the topical anesthetic fluid 20 through the dispensing nozzle 32 or conduit tip means 26 onto the surface area immediately in front of the advancing tip of the blade 14. Alternatively, the lever actuator means 38 can include a piston means 40 as shown in FIG. 4 which is adapted to compress a reservoir means 16. In this configuration movement of the actuator lever 38 will cause the piston to be urged into compressing contact against the reservoir 16 with the resulting expelling of topical anesthetic fluid therefrom. A connecting rod 42 may connect the piston member 40 to the lever portion of the lever actuator means 38. With the configuration shown in FIG. 4 the sleeve means 44 may be adapted to slide onto the top of the handle of a standardly configured laryngoscope 10 and in this fashion be detachable to facilitate repeated usage.

A spring biased retaining bar 46 is shown used in the configuration of FIG. 6 wherein the lever is movable forward and away from the reservoir 16. The spring biasing over pin 50 as the lever is moved inwardly the spring is compressed and the spring biased retaining bar 46 is caused to hold the reservoir in place such that the inwardly facing edge of the lever actuator means 38 can contact and compress the fluid chamber for dispensing of the fluid through supply conduit means 24.

FIGS. 1 and 2 show the simplest embodiment of the present invention which would be the most inexpensive and most readily acceptable. With this configuration a compressible outer wall area 36 is achieved by the formation of the walls of the reservoir means 16 to be of a pliable plastic. The reservoir is attached to the handle of a laryngoscope by a standardly configured plastic tie means and is readily attachable and detachable. The anesthetist can insert the blade while slowly compressing the reservoir on the handle and in this way dispense topical anesthetic in advance of the forwardly moving laryngoscope blade 14. The supply conduit means 24 is preferably held within a tubular retaining means 28 with this configuration. FIG. 2 shows the replaceable portion of this configuration.

FIG. 3 is an illustration of an alternative configuration for the reservoir means 16 wherein instead of a soft plyable pouch the reservoir takes the form of a compressible bellows-type configuration. This type of configuration can be placed in the removable sleeve shown in FIG. 4 and can be compressed by way of a lever actuator means 38. This sleeve as shown in FIG. 4 can be placed on and off of the handle portion of a laryngoscope for each usage.

FIGS. 5 and 6 show a configuration wherein a walled enclosure 48 is shown into which is placed the reservoir means 16. Upon movement downward of the lever 38 this enclosure is made smaller and as a result the topical anesthetic fluid is dispersed through the supply conduit means 24 for dispensing through the conduit tip means 26. In this configuration a spring biased retaining bar 46 is continuously in contact with the upper portion of the reservoir means 16 to hold it in place within the walled enclosure 48.

While particular embodiments of this invention have been shown in the drawings and described above, it will be apparent that many changes may be made in the form, arrangement and positioning of the various elements of the combination. In consideration thereof it should be understood that preferred embodiments of this invention disclosed herein are intended to be illustrative only and not intended to limit the scope of the invention.

We claim:

1. In laryngoscope having a blade and a handle, the improvement comprising means for applying topical anesthesia, said application means comprising:
    (a) a reservoir means for containing a predetermined amount of topical anesthetic fluid therein, said reservoir means defining a fluid chamber therein to hold the topical anesthetic fluid;
    (b) an attachment means for detachably securing said reservoir means directly to the handle of said laryngoscope;
    (c) a supply conduit means being attached to said reservoir means at a particular point and extending outwardly therefrom, said supply conduit means having two ends, one of which is at the point of attachment with respect to the reservoir means, said supply conduit means being in fluid flow communication with respect to said fluid chamber and adapted to receive topical anesthetic fluid therein for movement therealong;
    (d) a conduit tip means located at the end of said supply conduit means opposite from the point of attachment with respect to said reservoir means, said conduit tip means adapted to release topical anesthetic fluid received from said supply conduit means;
    (e) a retainer means attached with respect to said blade of said laryngoscope and detachably securing said supply conduit means with respect thereto;
    (f) a delivery means being engageable with respect to said reservoir means to compress said fluid chamber defined therein to cause the topical anesthetic fluid to be expelled from said fluid chamber through said supply conduit means for release through said conduit tip means.

2. The application means as defined in claim 1 wherein said delivery means comprises a compressible outer wall area of said reservoir means which is adapted to be compressed to expel topical anesthetic fluid therefrom through said supply conduit means.

3. The application means as defined in claim 1 wherein said supply conduit means as integral with said reservoir means.

4. The application means as defined in claim 1 wherein said retainer means comprises a tubular member secured with respect to said blade of said laryngoscope and receiving therein said supply conduit means.

5. The application means as defined in claim 1 further comprising a dispensing nozzle secured with respect to said blade of said laryngoscope and receiving said conduit tip means secured thereto to control the release of topical anesthetic fluid from said supply conduit means.

6. The application means as defined in claim 1 further comprising a lever actuator means pivotally secured with respect to said handle of said laryngoscope and adapted to pivot into abutting contact with respect to said reservoir means to expel topical anesthetic fluid from said fluid chamber defined therein.

7. The application means as defined in claim 6 wherein said lever actuator means includes a piston member in contact with respect to said reservoir means and adapted to compressibly expel topical anesthetic fluid from said fluid chamber upon movement of said lever actuator means.

8. The application means as defined in claim 7 further comprising a sleeve means selectively securable around said handle of said laryngoscope with said lever actuator means pivotally secured with respect to said sleeve means.

9. In a laryngoscpe having a blade and a handle, the improvement comprising means for applying topical anesthesia, said application means comprising:
    (a) a reservoir means for containing a predetermined amount of topical anesthetic fluid therein, said reservoir means defining a fluid chamber therein to hold the topical anesthetic fluid;
    (b) an attachment means for detachably securing said reservoir means directly to the handle of said laryngoscope;
    (c) a supply conduit means being integral with respect to said reservoir means and attached thereto at a particular point, said supply conduit means extending outwardly from said reservor means, said supply conduit means having two ends, one of which is at the point of attachment with respect to the reservoir means, said supply conduit means being in fluid flow communication with respect to said fluid chamber and adapted to receive topical anesthetic fluid therein for movement therealong;
    (d) a conduit tip means located at the end of said supply conduit means opposite from the point of attachment with respect to said reservoir means, said conduit tip means adapted to release topical anesthetic fluid received from said supply conduit means;

(e) a tubular retainer means attached with respect to said blade of said laryngoscope and receiving said supply conduit means extending therethrough;

(f) a delivery means being engageable with respect to said reservoir means to compress said fluid chamber defined therein to cause the topical anesthetic fluid to be expelled from said fluid chamber through said supply conduit means for release through said conduit tip means, said delivery means comprising a compressible outer wall area of said reservoir means for expelling topical anesthetic fluid when compressed; and (g) a dispensing nozzle secured with respect to said blade of said laryngoscope and adapted to receiving said conduit tip means secured thereto to control the release of topical anesthetic fluid from said supply conduit means.

10. A laryngoscope havng a means for applying topical anesthesia comprising:

(a) a blade means adapted to be placed into the throat area of a patient;

(b) a handle means secured with respect to said blade means to facilitate holding of said blade means during placement thereof;

(c) a reservoir means for containing a predetermined amount of topical anesthetic fluid therein, said reservoir means being detachably secured to said handle means, said reservoir means defining a fluid chamber therein to hold the topical anesthetic fluid;

(d) an attachment means detachably securing said reservoir means directly to said handle means;

(e) a supply conduit means being attached to said reservoir means at a particular point and extending outwardly therefrom, said supply conduit means having two ends, one of which is at the point of attachment with respect to the reservoir means, said supply conduit means being in fluid flow communication with respect to said fluid chamber and adapted to receive topical anesthetic fluid therein for movement therealong;

(f) a conduit tip means located at the end of said supply conduit means opposite from the point of attachment with respect to said reservoir means, said conduit tip means adapted to release topical anesthetic fluid received from said supply conduit means;

(g) a retainer means attached with respect to said blade means and detachably securing said supply conduit means with respect thereto;

(h) a delivery means being engageable with respect to said reservoir means to compress said fluid chamber defined therein to cause the topical anesthetic fluid to be expelled from said fluid chamber through said supply conduit means for release through said conduit tip means.

11. The laryngoscope as defined in claim 10 wherein said delivery means comprises a compressible outer wall area of said reservoir means which is adapted to be compressed to expel topical anesthetic fluid therefrom through said supply conduit means.

12. The laryngoscope as defined in claim 10 wherein said supply conduit means is integral with respect to said reservoir means.

13. The laryngoscope as defined in claim 10 wherein said retainer means comprises a tubular member secured with respect to said blade means and receiving therein said supply conduit means.

14. The laryngoscope as defined in claim 10 further comprising a dispensing nozzle secured with respect to said blade means and receiving said conduit tip means secured thereto to control the release of topical anesthetic fluid from said supply conduit means.

15. The laryngoscope as defined in claim 10 further comprising a lever actuator means pivotally secured with respect to said handle means of a laryngoscope and adapted to pivot into abutting contact with respect to said reservoir means to expel topical anesthetic fluid from said fluid chamber defined therein.

16. The laryngoscope as defined in claim 15 further including a spring biased retainer bar secured with respect to said lever actuator means to hold said reservoir means in contact with said handle means during movement of said lever actuator means.

* * * * *